(12) United States Patent
Armstrong (10) Patent No.: US 7,037,314 B2
(45) Date of Patent: May 2, 2006

(54) MULTIPLE BAND LIGATOR AND ANOSCOPE SYSTEM AND METHOD FOR USING SAME

(76) Inventor: David N. Armstrong, 7410 Princeton Trace, Atlanta, GA (US) 30328

(*) Notice: Subject to any disclaimer, the term of this patent is extended or adjusted under 35 U.S.C. 154(b) by 197 days.

(21) Appl. No.: 10/042,998

(22) Filed: Apr. 12, 2002

(65) Prior Publication Data

US 2002/0111639 A1    Aug. 15, 2002

Related U.S. Application Data

(60) Provisional application No. 60/260,724, filed on Jan. 9, 2001.

(51) Int. Cl.
*A61B 17/10* (2006.01)
(52) U.S. Cl. .................... 606/140; 606/1; 606/110
(58) Field of Classification Search ........ 606/205–209, 606/140–141, 110, 113, 139–142, 144–150, 606/148, 193, 1; 600/104, 184, 190, 194, 600/200, 201, 203, 208, 220, 224
See application file for complete search history.

(56) References Cited

U.S. PATENT DOCUMENTS

| | | | | |
|---|---|---|---|---|
| 2,184,642 | A * | 12/1939 | Glass | 607/113 |
| 3,997,085 | A * | 12/1976 | Lindquist | 222/326 |
| 4,257,419 | A * | 3/1981 | Goltner et al. | 606/140 |
| 4,690,132 | A * | 9/1987 | Bayer et al. | 600/219 |
| 5,158,563 | A * | 10/1992 | Cosman | 606/140 |
| 5,203,863 | A * | 4/1993 | Bidoia | 606/140 |
| 5,404,870 | A * | 4/1995 | Brinkerhoff et al. | 600/184 |
| 5,483,952 | A * | 1/1996 | Aranyi | 600/131 |
| 5,509,893 | A * | 4/1996 | Pracas | 600/224 |
| 5,741,273 | A * | 4/1998 | O'Regan | 606/140 |
| 5,788,715 | A * | 8/1998 | Watson et al. | 606/140 |
| 6,126,594 | A * | 10/2000 | Bayer | 600/184 |
| 6,136,009 | A | 10/2000 | Mears | 606/140 |
| 6,142,933 | A * | 11/2000 | Longo et al. | 600/184 |
| 6,610,070 | B1 * | 8/2003 | Tolkoff | 606/140 |
| 6,676,672 | B1 * | 1/2004 | Chu et al. | 606/139 |

FOREIGN PATENT DOCUMENTS

| | | | |
|---|---|---|---|
| EP | 1155660 | * | 11/2001 |
| WO | WO 9965400 | * | 12/1999 |

* cited by examiner

*Primary Examiner*—Glenn Dawson
*Assistant Examiner*—Michael Mendoza
(74) *Attorney, Agent, or Firm*—Thomas, Kayden, Horstemeyer & Risley, LLP (57) ABSTRACT

A hemorrhoidal ligator and anoscope system used to facilitate ligation of internal hemorrhoids. The ligating device consists of head, shaft and firing handle assemblies and is capable of storing and releasing multiple rubber bands singularly. The ligating device comprises an inner cylinder that is removable for disposal or reloading for reuse. The inner cylinder may also be configured with a disposable sleeve, the sleeve being disposable or capable of reloading. A modified loading cone is provided for facilitating loading of the rubber bands onto the inner cylinder or the inner cylinder sleeve 9. The anoscope is configured with three lateral apertures that coincide with the anatomic locations of the internal hemorrhoids in man and thus, simultaneously expose all three hemorrhoids for ligation and grading.

28 Claims, 5 Drawing Sheets

MULTIPLE BAND LIGATOR AND ANOSCOPE SYSTEM AND METHOD FOR USING SAME

CROSS-REFERENCE TO RELATED APPLICATION

This application claims priority to copending U.S. provisional application entitled, "Multiple Rubber Band Ligator," having Ser. No. 60/260,724, filed Jan. 9, 2001, which is entirely incorporated herein by reference.

TECHNICAL FIELD

The present invention is generally related to hemorrhoidal ligator and anoscope systems and, more particularly, is related to a system and method for ligation of internal hemorrhoids with a reloadable hemorrhoidal ligator and a configured anoscope.

BACKGROUND OF THE INVENTION

Rubber band ligation is widely used in medicine to entrap tissue in order to obliterate tissue or occlude blood vessels. Such applications consist of the utilization of "rubber bands" to strangulate and necrose tissue, such as internal hemorrhoids.

The principle of the rubber band ligator is well-known. In fact, the original hemorrhoidal ligating instrument (the Barron's bander) is still widely-used today. Although rubber band ligators are practical for treating hemorrhoids, most rubber band ligators can only hold and place one rubber band at a time. The Barons bander is a typical, "single shot" device and, thus, necessitates reloading of the instrument for application of each rubber band. Reloading the ligator is a time consuming and frustrating task which must occur while the patient is in an uncomfortable position. Thus, a major disadvantage of the typical ligator is the difficulty encountered in reloading the rubber bands.

Figure 1:
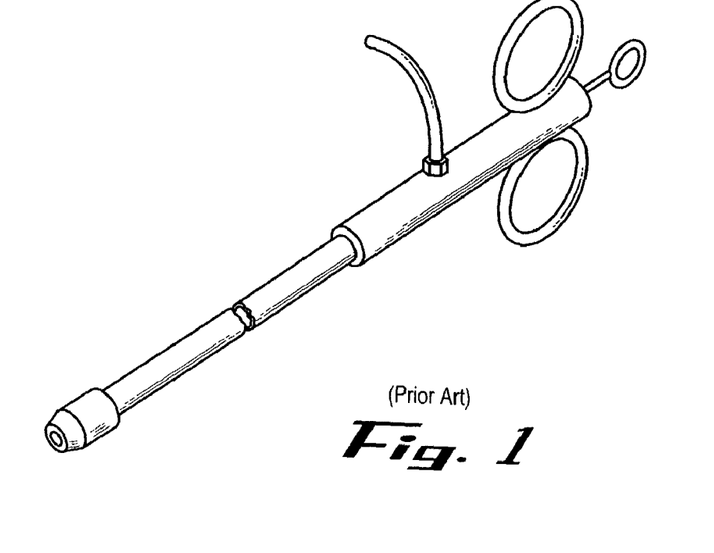
FIG. 1 is a prior art ligator.

In order to reduce the number of reloadings necessary during a hemorroidectomy, some ligator devices are configured to store and dispense a number of rubber bands. For example, in U.S. Pat. No. 6,136,009 to Mears, a ligating band dispenser is disclosed which stores multiple rubber bands and dispenses a single band at a time from a storage position to a release position (see FIG. 1). However, like many other devices intended to store and release multiple bands, the ligating band dispenser of the type taught by Mears can be bulky, difficult to hold and use particularly in conjunction with other instruments, difficult to position accurately, have an abundance of moving parts related to dispensing of bands, and have only a limited amount of space for storage of bands. Furthermore, if more rubber bands are needed than are preloaded on the Mears-type device, then the device must be retracted, reloaded and reinserted. These actions are likely to cause discomfort to the patient and may compromise the sterility of the procedure. Such factors tend to increase the complexity, cost, and size of the ligator devices and to decrease the reliability, reusability and maneuverability of the ligator devices.

Figure 2:
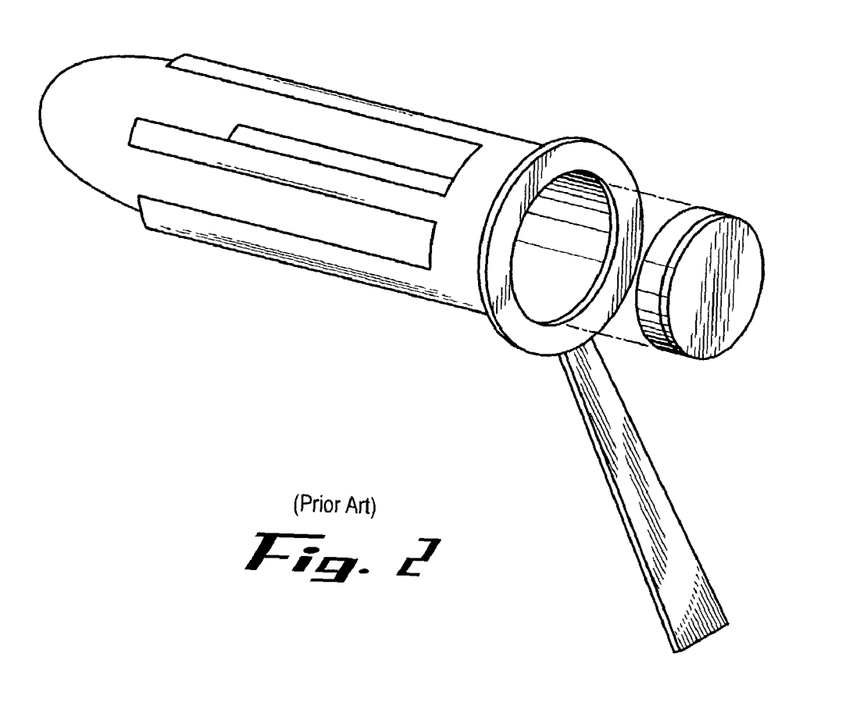
FIG. 2 is a prior art anoscope.

Conventionally, anoscopes have hollow cylindrical configurations and allow only limited access and viewing of internal hemorrhoid areas. For instance, as shown in U.S. Pat. No. 4,834,067 to Block, many anoscopes have only a single lateral aperture to provide exposure to a single internal hemorrhoid. As such, in order to gain access to and apply a rubber band to multiple internal hemorrhoids, the operator is required to retract and reinsert the anoscope multiple times. Some anoscopes are constructed of clear material to increase visibility, while some are configured with a plurality of apertures so as to attempt to provide better access to hemorrhoid areas. For example, in U.S. Pat. No. 6,126,594 to Bayer, an anoscope is provided which has a plurality of annularly spaced apertures that allow simultaneous access to multiple hemorrhoid areas (see FIG. 2). Although Bayer may reduce the number of times that insertion of the anoscope is required, the plurality of apertures in this type of anoscope must be aligned so as to properly expose the hemorrhoids, and if adjustment is required for access to an internal hemorrhoid, unnecessary discomfort may result.

Thus, a heretofore unaddressed need exists in the industry to address the aforementioned deficiencies and inadequacies and to provide a ligator and anoscope system that provides access to the locations of multiple internal hemorrhoids and simultaneously supplies multiple rubber bands for ligation of multiple hemorrhoids without necessitating multiple retractions and reinsertions of the ligator and anoscope.

SUMMARY OF THE INVENTION

The present invention provides a system and method for ligation of internal hemorrhoids. Briefly described, in architecture, one embodiment of the apparatus, among others, can be implemented as follows.

A system for ligating hemorrhoids includes a reloadable, multiple rubber band ligating device having head, shaft and handle assemblies and a three-apertured anoscope.

The head assembly of the ligating device includes two concentric cylinders, telescopically slidably opposed over each other so that the outer cylinder surrounds the inner cylinder. The inner cylinder is detachably connected to a central rod of the shaft assembly. The inner cylinder is designed to be removable from the ligating device and is further configured to accommodate the premounting of one or more rubber bands upon it. The central rod passes through an aperture in a firing handle and is secured to the firing handle by means of a spring clip or ratchet mechanism located in relation to the firing handle aperture. In this manner, the inner cylinder can be removed and replaced with another preloaded inner cylinder while the ligating device is in use without retraction of the entire ligating device.

In an alternative embodiment, the inner cylinder is modified to incorporate a shoulder against which a replaceable inner cylinder sleeve may be abutted. Thus, the inner cylinder is surrounded with a disposable sleeve upon which the multiple rubber bands can be mounted. In this manner, the inner cylinder itself is not replaced; instead, the inner cylinder sleeves which surround the inner cylinder are replaced, thus producing a reusable multiple rubber band ligator device. The use of a disposable inner cylinder sleeve is very cost effective as it reduces the amount of material for the ligator device that must be sterilized or thrown away.

The shaft assembly comprises a central rod, which is slidably enclosed within a surrounding outer rod. The central rod is detachably connected (e.g. by a screw and threading) to the inner cylinder of the head assembly, and the outer rod is affixed to the outer cylinder. In one embodiment of the device, the central rod passes through an aperture in the proximal aspect of the firing handle and is secured to the firing handle by means of a "V" or "N" shaped spring clip or ratchet mechanism located in relation to the aperture. By activating the firing handle, the central rod is retracted and the inner cylinder is withdrawn within the outer cylinder. As the inner cylinder is retracted within the outer cylinder, rubber bands are released from the end of the inner cylinder and ligate the targeted tissue.

To reload or replace the inner cylinder, the spring clip or ratchet is released. The central rod is then pushed forward, the inner cylinder detached from the central rod and a new inner cylinder attached. In this manner, one or more rubber bands are premounted on the new inner cylinder of the head assembly, such that after each firing, the inner cylinder is replaced by a preloaded inner cylinder. The central rod is then pulled back and the inner cylinder slid within the outer cylinder. The spring clip or ratchet is then re-engaged back to its original position prior to firing. This configuration provides the ability to reload the ligator by a simpler and less time consuming method.

In one embodiment of the ligator, forceps may be passed through the head assembly and used to grasp hemorrhoidal tissue for ligation. Alternatively, tissue may be aspirated into the head of the instrument by suction applied via a suction channel in the central rod, which communicates with the head assembly. It is anticipated that in enclosing the head of the instrument to make it airtight, one may use a magnifying lens to optimize visualization of the anal canal and hemorrhoidal areas. Having aspirated tissue into the instrument head, the firing handle is activated and the tissue is ligated.

Furthermore, a cylindrical anoscope is utilized to expose all three internal hemorrhoids simultaneously. The anoscope is configured for telescopically receiving the ligator device in that the anoscope is a hollow, tapering cylinder, with three apertures located on its distal aspect. These apertures are located at the three, seven and eleven o'clock positions, which are the normal anatomic location of internal hemorrhoids in man (in the prone position). Thus, the anoscope is configured to expose all three internal hemorrhoids simultaneously. In this respect, having once inserted the anoscope and removed the central obturator, all three internal hemorrhoids are accessible by virtue of the location of the lateral apertures in the anoscope to a ligator device which is inserted through the hollow cylinder of the anoscope. Thus, ligation of the internal hemorrhoids is facilitated by means of the multiple ligator or other instrument (e.g. infra-red coagulator, stapling device or cryo-ablation), and discomfort from repeated insertions is minimized. The anoscope of the present invention may also be used to quantitatively grade hemorrhoids as the apertures provide a means of comparing the sizing of the internal hemorrhoids.

The present invention can also be viewed as providing methods for accessing and ligating internal hemorrhoids. In this regard, one embodiment of such a method, among others, can be broadly summarized by the following steps: insertion of anoscope in alignment with the three, seven and eleven o'clock positions; isolating the internal hemorrhoids; retraction of tissue to be ligated; application of rubber bands onto tissue using a multiple band ligator device; reloading of the ligator device if necessary; and retraction of the ligator and anoscope.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 3 is a perspective view of the head assembly, showing detachable inner cylinder and premounted rubber band(s);

FIG. 7 is a side view of the multiple band ligator.

DETAILED DESCRIPTION OF THE PREFERRED EMBODIMENT

As shown in FIG. 3 a hemorrhoidal ligator device for applying multiple rubber bands to desired tissue includes a head assembly 10 for protrusion into the internal cavities of a life form, where the head assembly 10 includes an inner cylinder 12 and an outer cylinder 11 arranged in telescopic slidable relationship with respect to each other. The inner cylinder 12 includes an end portion that protrudes beyond the outer cylinder 11 and which inner cylinder 12 is preloaded with a plurality of rubber bands 13. The outer cylinder 11 has an inner dimension for engaging the rubber bands 13 mounted on the end portion of the inner cylinder 12 such that the rubber bands are urged off the end portion of the inner cylinder 12 when said outer cylinder 11 is slid about the inner cylinder 12.

The ligator device further comprises a shaft assembly 30 including a central rod 14 having a first end connected to the inner cylinder 12 and a second end for protruding out beyond the internal aspects of a life form. The outer rod 17 has a first end rigidly connected to the outer cylinder 11 of the head assembly 10 and a second end for protruding out beyond the internal aspects of the life form. In this regard, the inner cylinder 12 and outer cylinder 11 can be manipulated internal to the life form by movement of the central rod 14 with respect to the outer rod 17 of the shaft assembly 30 from outside the life form.

Figure 4:
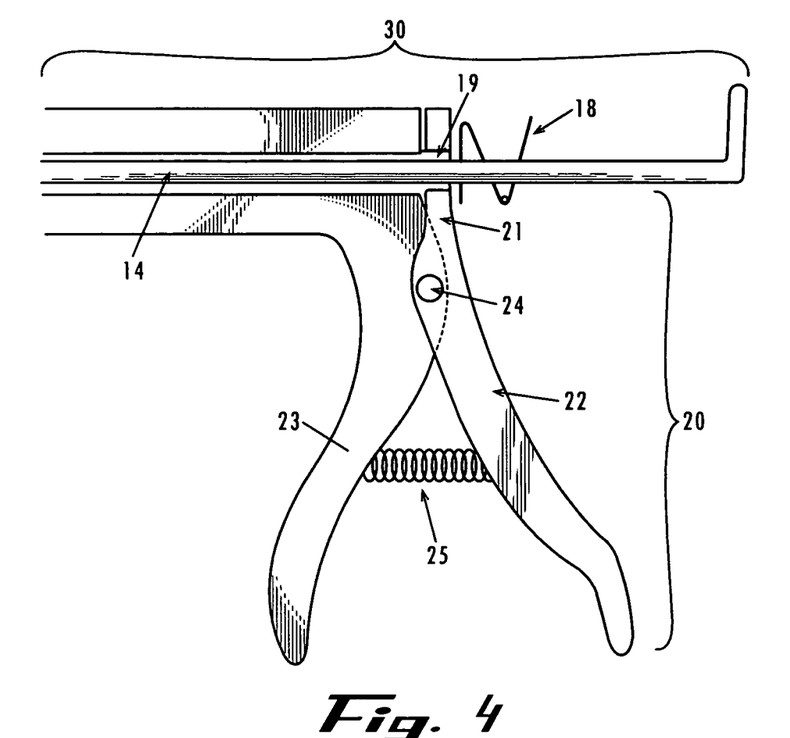
FIG. 4 is a side view of the firing handle mechanism and central rod configuration and is a continuation of FIG. 3.

As shown in FIG. 4 the ligator device further includes a handle assembly 20 mounted to the second ends of the central rod 14 and the outer rod 17 for use in manipulating the inner cylinder 12 and outer cylinder 11. Thus, the ligator device of the present invention consists of three basic parts: a head assembly 10, handle assembly 20 and shaft assembly 30.

As shown in FIG. 3, the head assembly 10 of the ligator is comprised of two concentric cylinders 11, 12. The outer cylinder 11 of the head is slidably disposed about the inner cylinder 12. One or more rubber bands 13 are premounted on the inner cylinder 12. With this configuration, the rubber bands 13 are, therefore, located on the same circumferential plane as the outer cylinder 11. As the inner cylinder 12 is withdrawn through the outer cylinder 11, the rubber bands 13 are forced from the inner cylinder 12 and onto tissue drawn within the head assembly 10. In this manner, the tissue is ligated.

As further shown in FIG. 3, the inner cylinder 12 is detachably affixed to a central rod 14. In one embodiment, the length of the central rod may be approximately between 6 and 8 inches; however, it is anticipated that the length of the central rod or overall length of the ligator device may be adjusted. In a preferred embodiment, a screw 15 and thread 16 attachment is used to detachably affix the inner cylinder 12 and the central rod 14; however, any means of detachably affixing the central rod 14 to the inner cylinder 12 may be used. The inner cylinder 12 of the head assembly 10 connects to the central rod 14, while the outer cylinder 11 is secured to the outer rod 17. In a preferred embodiment, the outer cylinder 11 is fixedly attached to the outer rod 17; however the outer cylinder 11 and the outer rod may be detachably secured in an alternative embodiment. In this manner, as the firing handle is activated, the inner cylinder 12 is retracted rearward and withdrawn within the outer cylinder 11.

In one embodiment, the inner cylinder 12 is configured to be removed and reloaded with additional multiple rubber bands 13. In another embodiment, the inner cylinder 12 is configured to be removed and replaced with another preloaded replacement inner cylinder. In a further embodiment, the inner cylinder 12 is configured to be removable and is further configured with a shoulder against which a disposable inner cylinder sleeve 9 is abutted. In this manner, the disposable inner cylinder sleeve 9 is opposed about the inner cylinder 12 and another preloaded disposable inner cylinder sleeve 9 may be used to replace the disposable sleeve after firing. That is, the disposable inner cylinder sleeve 9 is configured with multiple rubber bands 13 upon it and is replaced after firing with another disposable inner cylinder sleeve 9.

Referring to FIG. 4, the handle 20 and shaft 30 assemblies are shown. In one embodiment of the present invention, the central rod 14 passes through an aperture 19 in the proximal aspect of the firing handle 21. Immediately posterior to the aperture 19, the central rod 14 passes through an opening in a leaf spring 18, which secures the central rod 14 in place during firing of the ligator.

It is anticipated that other alternative configurations of the spring clip 18 may be include any means of temporarily securing the central rod 14 to the firing handle 21 mechanism. By way of example, as shown in FIG. 7, the spring clip 18 may be replaced with serrations 74 along the central rod 14. In this manner, pulling the firing handle 21 withdraws the rod 14 by means of a ratchet mechanism. In the ratchet configuration, a first spring 72 is used to draw the serrated central rod 14 rearward and a second spring 18 is used to stabilize and prevent forward slippage of the central rod 14.

In one configuration of the present invention, the handle assembly 20 includes a firing handle 21 having two opposing grips 22 and 23, a pivot 24 and a spring 25. The firing handle 21 is articulated by means of a pivot 24, and is returned to the original position after firing by means of a spring 25 located within the grips 22, 23. During firing, the central rod 14 is retracted by the firing handle 21 by means of a slidable spring clip 72 and ratchet serrations 74, which secures the central rod 14 to the firing handle 21 during firing. The central rod 14 is retracted by activating the firing handle 21 by the two opposing grips 22 and 23. Retraction of the central rod 14 causes the inner cylinder 12 to retract and forces the rubber bands 13 off the end of the inner cylinder 12.

To reload the inner cylinder 12, the spring clip 18 or ratchet mechanism is disengaged from central rod 14, so releasing the central rod 14. The central rod 14 may then be advanced forward and the inner cylinder 12 may be detached for reloading or replacement. The inner cylinder 12 may then be detached and replaced with a preloaded cylinder or reloaded. Once the inner cylinder 12 is replaced, the central rod 14 is returned to its original position, and the spring 18 and pawl 72 are re-engaged with the ratchet mechanism back to their original positions prior to firing.

Figure 6:
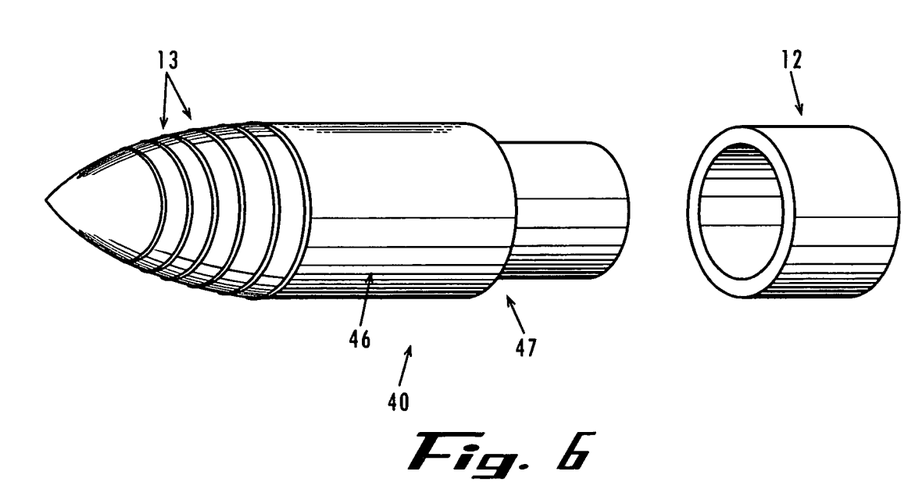
FIG. 6 is a perspective view of a modified loading cone.

As shown in FIG. 6, a modified loading cone 40 is used to preload the inner cylinder 12 or the disposable inner cylinder sleeve 9. In this manner, the inner cylinder 12 or the disposable inner cylinder sleeve 9 of the head assembly 10 may be reloaded with multiple rubber bands 13 using the modified loading cone.

In application, tissue that is to be ligated will be drawn into the head assembly 10 of the ligating device by using either grasping forceps or a suction mechanism. The grasping forceps are passed through the head assembly 10, and tissue is grasped and retracted into the head of the instrument. Alternatively, a suction mechanism may be utilized to draw tissue within the head of the instrument. While the tissue is retracted, the ligating device is fired and one or more bands are secured around the tissue. In this manner, the tissue is ligated.

If a suction mechanism is utilized, this embodiment consists of a hollow central rod 14, which transmits suction pressure from an external source, to the head of the ligating device. In this embodiment, the head assembly 10 is modified by enclosing the rear aspect of the head assembly 10 with a clear plastic disc or lens, to render the head assembly into a closed, airtight system. In another embodiment, the clear plastic disc or lens that is used to enclose the head assembly may be a magnifying lens that optimizes visualization of the anal canal and hemorrhoidal areas. Suction is transmitted to the ligating device via flexible suction tubing, which detachably affixes to the rear aspect of the hollow central rod 14. Alternatively, an internal suction source may be configured into the ligating device by, for example, the incorporation of a suction bulb into the device. By activating and releasing the suction bulb, suction is generated which aspirates tissue into the head of the ligating device for appropriate ligation with the bands 13.

Although the present ligating device has been described for use in ligation of internal hemorrhoids, it is anticipated that this device may be useful for other applications involving the banding of tissue with a ligating device, such as, but not limited to esophageal varices, hemorrhages, etc.

The present ligator device facilitates reloading the rubber band dispenser, reduces or eliminates the need to retract and reinsert the anoscope and ligator into the patient, easily facilitates accurate placement of one or more rubber bands about tissue to be ligated, and utilizes a simple design to dispense the bands one at a time. Compared with other multiple band ligator devices, the present ligator is inexpensive and is substantially, if not completely, re-useable because of the reloadable or replaceable inner cylinder or disposable inner cylinder sleeve 9.

In performing a hemorrhoidectomy using the banding procedure, it is necessary to insert an anoscope to expose the hemorrhoids in the anal canal. In man, the three internal hemorrhoids are located at fairly constant locations within the anal canal: left lateral, right anterior and right posterior positions. These positions are equivalent to the three, seven and eleven o'clock locations, with the patient in the prone position. Other, prior art, anoscopes are configured to either expose only one hemorrhoid location at a time or are configured with a plurality of apertures. With an anoscope having only one aperture, the placement of the anoscope must be precise and movement to expose other hemorrhoids requires the retraction and reinsertion of the device. For anoscopes having a plurality of apertures, careful placement is also required to expose as many of the multiple hemorrhoids as possible. Imprecise placement of the prior art anoscopes requires retraction and reinsertion or adjustment of the device internally, both of which are time consuming and result in discomfort to the patient.

Figure 5A:
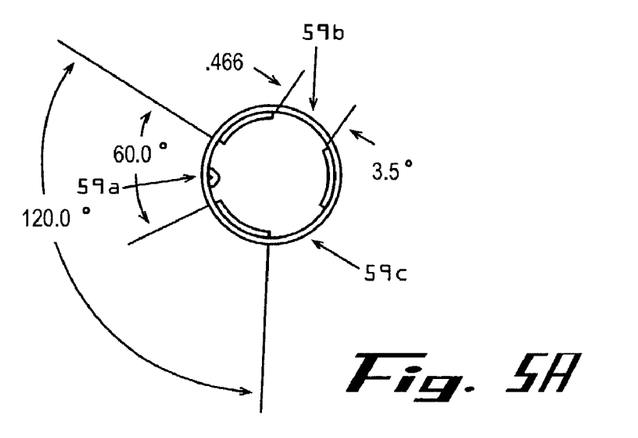
FIG. 5A is an end view of the anoscope showing the three apertures at the three, seven and eleven o'clock positions.
Figure 5B:
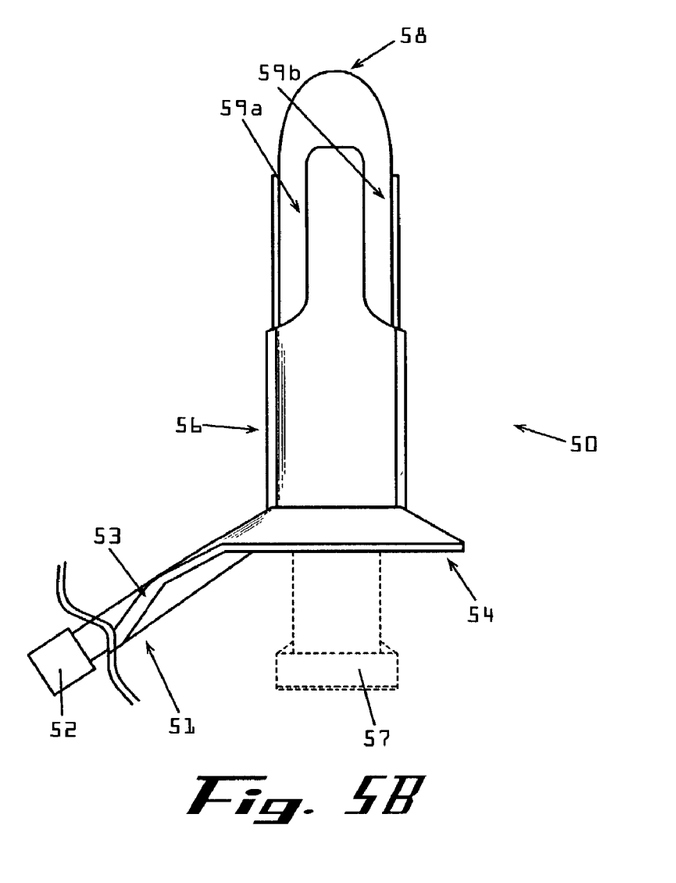
FIG. 5B is a side view of the anoscope showing the three longitudinal apertures located at the normal anatomic sites of the three internal hemorrhoids in man.

The three-aperture configuration of the present anoscope 50 addresses the deficiencies of the prior art. Referring to FIGS. 5A and 5B, the present anoscope 50 is comprised of a hollow cylinder 56, tapered at its distal aspect for ease of insertion. A central removable obturator 57 extends beyond the distal tip of the anoscope 50, for ease of insertion. The obturator 57 is made of a smooth, low-friction material and has a smooth, rounded tip 58 to permit easy introduction of the anoscope 50. Having introduced the anoscope 50, the obturator 57 is removed to permit examination of and access to the internal hemorrhoids.

As shown in FIG. 5A, at its distal aspect, the anoscope 50 has three lateral apertures 59a, b, c, located at the three, seven and eleven o'clock positions. The lateral apertures 59a, b, c coincide with the normal anatomic location of the internal hemorrhoids in a patient in the prone position. Thus, using the present anoscope 50, a single insertion of the anoscope therefore allows simultaneous access to all three internal hemorrhoids. The three lateral apertures 59a, b, c extend in a longitudinal direction, in the plane of the anoscope 50 and extend approximately half-way along the length of the anoscope 50. In one configuration of the current device the width of the apertures is equal to one sixth of the total circumference of the tip of the anoscope, In this configuration, the combined width of the three apertures is equal to one half of the circumference of the tip of the anoscope.

A flange or shoulder 54 is located at the proximal aspect of the anoscope 50 so as to optimize exposure of the anal canal and to facilitate visualization through the anoscope 50. A handle 51 extends from the proximal flange or shoulder 54 and extends at an angle away from the axis of the anoscope 50. This handle 51 provides a means of inserting, withdrawing and rotating the anoscope. The handle 51 incorporates a housing 52 for the attachment of an external light source and a fiber optical cable or rod 53 which transmits the light from the external source, into the lumen of the anoscope 50 for the purpose of illuminating the interior of the anal canal.

The location of the handle 51 in relation to the anoscope 50 may be in the twelve o'clock or six o'clock positions in order to assure proper positioning of the apertures of the anoscope to the corresponding hemorrhoid locations in man. When the handle 51 is configured in the twelve o'clock position relative to the anoscope 50, the apertures 59a, b, c of the anoscope 50 are correctly oriented in relation to the internal hemorrhoids for a patient in the prone position. When, alternatively, the handle 51 is configured in the six o'clock position, the apertures 59a, b, c of the anoscope 50 are correctly oriented in relation to the internal hemorrhoids for a patient in the supine position.

The present anoscope also makes it possible to quantitatively grade internal hemorrhoids. Internal hemorrhoids are currently graded according to patient history as: Grade I, no prolapse; Grade II, spontaneous reduction after prolapse; Grade III, requiring manual reduction after prolapse; Grade IV, prolapsed and irreducible. This method is subjective, qualitative and dependent upon individual patient interpretation. Using the current anoscope, specifically with each of three apertures comprising one sixth of the anoscope circumference, it is possible to grade internal hemorrhoids in a quantitative manner. Internal hemorrhoids may be graded as: Grade I, extending <0.5 of the radius of the anoscope; Grade II extending >0.5 of the radius and Grade III extending >1.0 of the radius i.e. contact between two or three hemorrhoids at the center of the anoscope. Grade IV (prolapsed and irreducible) remains unchanged from the previous system. Thus, the present anoscope provides an objective and quantitative method of grading internal hemorrhoids and represents an improvement over the previous method.

Reference is made to FIG. 6 showing a modification of a conventional loading cone. Loading cones are used to load rubber bands 13 onto prior art ligating instrunents. The conventional loading cone has been modified to facilitate the preloading of multiple rubber bands 13 on the detachable inner cylinder 12 or the disposable inner cylinder sleeve 9 using a modified loading cone 40. The loading cone 40 incorporates a shouldered mandrel 47, at the rear aspect of the cone 40, and a tapered front section 46 for ease in maneuvering the rubber bands 13 onto the cone 40. The diameter of the interior of the inner cylinder 12 is greater than that of the exterior of the mandrel of the shouldered mandrel 47 such that the inner cylinder 12 of the current ligating device slides into the shouldered mandrel 47, and multiple rubber bands 13 may be slid over the loading cone 40 and onto the inner cylinder 12. In this respect, the diameter of the shouldered mandrel 47 should be less than that of the greatest diameter of the tapered front section 46 of the loading cone 40. Additionally, the diameter of the inner cylinder 12 should be equivalent to or less than the greatest diameter of the loading cone 40 such that the rubber bands 13 are transitioned easily from the loading cone 40 onto the inner cylinder 12. Once the inner cylinder 12 is loaded with rubber bands 13, the inner cylinder 12 is detached from the cone 40 and is ready for attachment onto the ligator device prior to firing.

The preferred method for treating internal hemorrhoids using the rubber band ligator and anoscope 50, involves introducing the anoscope 50 and obturator 57 into the anal canal. When the obturator 57 is removed, all three internal hemorrhoids are exposed in their usual anatomic location, through the lateral apertures 59a, b, c of the anoscope 50. In conjunction with the multiple band hemorrhoidal ligator, all three internal hemorrhoids can be ligated without re-introducing the anoscope 50. Furthermore, the ligator by virtue of its removable inner cylinder 12, may be quickly reloaded with multiple rubber bands if necessary without removing the anoscope and without significant delay associated with single band devices. Thus, this technique, comprising the system of the three-apertured anoscope and rubber band ligator described herein, renders the hemorroidectomy procedure simpler, faster and less painful for the patient.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following is claimed:

1. A system for ligation of internal hemorrhoids in the anal canal with the hemorrhoids at the traditional anatomical positions of the hemorrhoids in the human body, comprising:
an anoscope, a multiple rubber band ligator device and a loading cone device,
said anoscope is configured with an elongated cylinder having a distal end for insertion in an anal canal and a proximal end for positioning at the entrance of the anal canal with three multiple apertures formed about the cylinder and extending from said distal end along approximately one-half the length of the cylinder at positions about the hollow cylinder for simultaneously exposing hemorrhoids in the anal canal at the normal anatomic locations of the hemorrhoids in a patient without repositioning the anoscope and permitting simultaneous access through said apertures to the normal locations for internal hemorrhoids of the anal canal, and presenting the non-apertured portion of the cylinder to the entrance to the anal canal;
a handle mounted to said cylinder at a predetermined position with respect to said apertures such that by orienting said handle with respect to the patient the apertures are oriented at the anatomical positions of hemorrhoids of the patient,
wherein the ligator device is configured to store multiple rubber bands on an inner cylinder and further configured to release a single rubber band at a time from the inner cylinder; and
wherein the modified loading cone is configured for attachment to the removable inner cylinder to facilitate loading of rubber bands onto said inner cylinder.

2. The system of claim 1, wherein
said apertures of said anoscope each have a width approximately equivalent to one-sixth of the circumference of the cylinder of the anoscope, and
said three apertures being spaced apart about said cylinder to be at the three o'clock, seven o'clock and eleven o'clock positions about the cylinder when the cylinder is inserted in the anal canal with the handle oriented in the twelve o'clock position.

3. The system of claim 1, wherein the ligator device is comprised of an inner cylinder, an outer cylinder, a central rod, an outer rod, and a firing handle.

4. The system of claim 3, wherein the inner cylinder and the outer cylinder are detachably affixed, the outer cylinder and the outer rod are fixedly attached, and the central rod is secured to the firing handle, such that movement of the firing handle withdraws the central rod, which in turn withdraws the inner cylinder and a single rubber band is released from the inner cylinder.

5. The system of claim 3, wherein the inner cylinder is configured for removal for reloading with multiple rubber bands and replacement within the ligator device for reuse.

6. The system of claim 3, wherein the inner cylinder is configured for removal after firing of said multiple rubber bands and replacement with another preloaded inner cylinder.

7. The system of claim 3, wherein the inner cylinder is configured with a shoulder against which a disposable inner cylinder sleeve is abutted;
the disposable inner cylinder sleeve configured to surround said inner cylinder;
the disposable inner cylinder sleeve configured with one or more premounted rubber bands; and
the disposable inner sleeve configured for removal and replacement after firing of the rubber bands with another preloaded disposable inner cylinder sleeve.

8. The system of claim 4, wherein the central rod is secured to the firing handle with a spring clip, so that when the spring clip is released, the central rod is retracted and the inner cylinder is withdrawn within the outer cylinder and rubber bands are released from the inner cylinder.

9. The system of claim 4, wherein the central rod is secured to the firing handle with a ratcheting mechanism, said ratcheting mechanism comprising serrations along a proximal end of the central rod, a first spring used to withdraw the serrated central rod and a second spring used to stabilize and prevent forward slippage of the central rod, so that when the firing handle is activated, the central rod is retracted and the inner cylinder is withdrawn within the outer cylinder and rubber bands are released from the inner cylinder.

10. The system of claim 4, wherein the loading cone is configured with a tapered front section and a shouldered recess which receives the inner cylinder to facilitate the loading of multiple rubber bands onto the inner cylinder.

11. A system for ligation of internal hemorrhoids comprising:
an anoscope,
a multiple rubber band ligator device, and
a loading device for loading rubber bands on said ligator device,
said ligator device being configured to store multiple rubber bands on an inner cylinder and further configured to release a single rubber band at a time from the inner cylinder;
said loading device being configured for loading of rubber bands onto said inner cylinder,
said anoscope including a cylinder having a distal end for insertion in the anal canal and a proximal end for positioning exteriorly of the anal canal,
said cylinder defining three lateral apertures extending along said cylinder opening from the distal end of said cylinder toward the proximal end of the cylinder,
said apertures being spaced apart about said cylinder to be positionable at the three o'clock, seven o'clock and eleven o'clock positions about the cylinder when inserted in the anal canal with the patient in the supine position, and
said lateral apertures each being one-sixth of the circumference of the cylinder such that the sizes of the hemorrhoids can be visually graded by the observer by the degree of extension of the hemorrhoids from outside the cylinder through the apertures of the anoscope.

12. The system of claim 11, wherein said cylinder is tapered at its distal end.

13. The system of claim 11, wherein said apertures extend approximately half-way along the length of said cylinder.

14. The system of claim 11, wherein said apertures extend not more than half-way along the length of said cylinder to expose only internal hemorrhoids in the anal canal.

15. The system of claim 11, and further including a flange extending radially from the proximal end of said cylinder.

16. The system of claim 15, and further including a handle extending from said flange, said handle oriented with respect to said cylinder to be positioned at the twelve o'clock position when said apertures are at the three o'clock, seven o'clock and eleven o'clock positions about the cylinder and when inserted in the anal canal with the patient in the supine position.

17. The system of claim 16, wherein said handle incorporates a housing for the attachment of an external light source and a fiber optic cable that transmits light into the cylinder of said anoscope.

18. The system of claim 16, wherein said handle is oriented on said flange to be in the six o'clock position when the openings in the cylinder are oriented in the nine o'clock, one o'clock and five o'clock positions with the patient in the prone position.

19. In combination with a ligator and a loading device, an anoscope for ligation of internal hemorrhoids comprising:
a cylinder having a distal end for insertion in the anal canal and a proximal end for positioning exteriorly of the anal canal,
said cylinder defining three lateral apertures opening from the distal end of said cylinder toward the proximal end of said cylinder, said apertures being spaced apart about said cylinder to be positionable at the three o'clock, seven o'clock and eleven o'clock positions about the cylinder when inserted in the anal canal with the patient in the supine position for exposing three areas of the anal canal that have internal hemorrhoids,
said apertures being formed at a predetermined size to observe the size of the hemorrhoids by the extension of the hemorrhoids from outside said cylinder and through the apertures,
wherein said apertures extend approximately half-way along the length of said cylinder to expose enternal hemorrhoids while the rest of the cylinder tends to hold other features of the anal canal outside the cylinder, and
visual means at said proximal end of said cylinder for visually rotatively orienting said anoscope with the apertures of said cylinder oriented in the anal canal with the apertures in registration with the hemorrhoid positions of man.

20. The combination of claim 19, and wherein said visual means comprises a handle.

21. The combination of claim 19, wherein said cylinder is tapered at its distal end.

22. In combination with a ligator and a loading device, an anoscope for ligation of internal hemorrhoids comprising:
a cylinder having a distal end for insertion in the anal canal and a proximal end for positioning exteriorly of the anal canal,
said cylinder defining three lateral apertures opening from the distal end of said cylinder toward the proximal end of said cylinder, said apertures being spaced apart about said cylinder to be positionable at the three o'clock, seven o'clock and eleven o'clock positions about the cylinder when inserted in the anal canal with the patient in the supine position for exposing three areas of the anal canal that have internal hemorrhoids,
said apertures being formed at a predetermined size to observe the size of the hemorrhoids by the extension of the hemorrhoids from outside said cylinder and through the apertures,
visual means at said proximal end of said cylinder for visually rotatively orienting said anoscope with the apertures of said cylinder oriented in the anal canal with the apertures in registration with the hemorrhoid positions of man,
wherein said apertures extend not more than half-way along the length of said cylinder to expose only internal hemorrhoids in the anal canal.

23. The combination of claim 19, and further including a flange extending radially from the proximal end of said cylinder.

24. The combination of claim 23, wherein said handle extends from said flange.

25. The combination of claim 24, wherein said handle incorporates a housing for the attachment of an external light source and a fiber optic cable that transmits light into the cylinder of said anoscope.

26. In combination with a ligator and a loading device, an anoscope for ligation of internal hemorrhoids comprising:
a cylinder having a distal end for insertion in the anal canal and a proximal end for positioning exteriorly of the anal canal,
said cylinder defining three lateral apertures opening from the distal end of said cylinder toward the proximal end of said cylinder, said apertures being spaced apart about said cylinder to be positionable at the three o'clock, seven o'clock and eleven o'clock positions about the cylinder when inserted in the anal canal with the patient in the supine position for exposing three areas of the anal canal that have internal hemorrhoids,
said apertures being formed at a predetermined size to observe the size of the hemorrhoids by the extension of the hemorrhoids from outside said cylinder and through the apertures,
visual means at said proximal end of said cylinder for visually rotatively orienting said anoscope with the apertures of said cylinder oriented in the anal canal with the apertures in registration with the hemorrhoid positions of man,
a flange extending radially from the proximal end of said cylinder,
a handle extending from said flange,
said handle being oriented on said flange to be in the six o'clock position when the openings in the cylinder are oriented in the nine o'clock, one o'clock and five o'clock positions with the patient in the prone position.

27. In combination with a ligator and a loading device, an anoscope for ligation of internal hemorrhoids comprising:
a cylinder having a distal end for insertion in the anal canal and a proximal end for positioning exteriorly of the anal canal,
said cylinder defining three lateral apertures opening from the distal end of said cylinder toward the proximal end of said cylinder, said apertures being spaced apart about said cylinder to be positionable at the three o'clock, seven o'clock and eleven o'clock positions about the cylinder when inserted in the anal canal with the patient in the supine position for exposing three areas of the anal canal that have internal hemorrhoids,
said apertures being formed at a predetermined size to observe the size of the hemorrhoids by the extension of the hemorrhoids from outside said cylinder and through the apertures, visual means at said proximal end of said cylinder for visually rotatively orienting said anoscope with the apertures of said cylinder oriented in the anal canal with the apertures in registration with the hemorrhoid positions of man,
wherein said openings in said cylinder each extend about said cylinder approximately $\frac{1}{6}$ of the cylinder circumference.

28. In combination, a ligator, a loading device for loading bands on the ligator, and an anoscope for receiving the ligator for ligation of internal hemorrhoids of the anal canal of a patient, the anoscope including:

a cylinder having a distal end for insertion in the anal canal and a proximal end for positioning exteriorly of the anal canal, said cylinder defining three lateral apertures opening about one-half the distance from the distal end of said cylinder toward the proximal end of said cylinder, said three apertures being spaced apart about said cylinder to register with the internal hemorrhoids in the normal anatomic location of man, a handle extending radially away from the proximal end of the cylinder at a predetermined angle with respect to the apertures of the cylinder such that when the cylinder is inserted in the anal canal of the patient and the handle is oriented at a predetermined attitude with respect to the patient the apertures of the cylinder register with the internal hemorrhoids of the patient.

* * * * *